(12) United States Patent
Goodale et al.

(10) Patent No.: US 6,627,156 B1
(45) Date of Patent: Sep. 30, 2003

(54) CAP PIERCING STATION FOR CLOSED CONTAINER SAMPLING SYSTEM

(75) Inventors: David L. Goodale, Yorba Linda, CA (US); William M. Robins, La Habra, CA (US); Steven P. Katzmann, Yorba Linda, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 568 days.

(21) Appl. No.: 09/599,305

(22) Filed: Jun. 22, 2000

(51) Int. Cl.[7] .............................................. G01N 35/10
(52) U.S. Cl. .......................... 422/99; 220/277; 30/353; 73/864.41
(58) Field of Search ........................ 422/99, 102, 100; 220/267, 277; 30/353; 73/864.41, 863.85, 864.24

(56) References Cited

U.S. PATENT DOCUMENTS

| | | | |
|---|---|---|---|
| 3,848,579 A | * 11/1974 | Villa-Real ................... 600/577 |
| 3,883,305 A | 5/1975 | Hoskins et al. |
| 3,991,627 A | * 11/1976 | Laird et al. ............... 73/864.16 |
| 4,110,875 A | 9/1978 | Foster |
| 4,729,876 A | 3/1988 | Hennessy et al. |
| 4,745,068 A | 5/1988 | Godrey et al. |
| 4,808,381 A | * 2/1989 | McGregor et al. .......... 422/100 |
| 4,862,753 A | * 9/1989 | Lovette et al. ............ 73/863.23 |
| 4,871,682 A | 10/1989 | Mazza |
| 4,951,512 A | * 8/1990 | Mazza et al. ............... 73/864.23 |
| 4,974,457 A | * 12/1990 | Angst et al. .............. 73/863.81 |
| 5,081,872 A | * 1/1992 | Greter ..................... 73/864.74 |
| 5,216,926 A | 6/1993 | Lipscomb |
| 5,236,666 A | 8/1993 | Hulette et al. |
| 5,327,901 A | * 7/1994 | Delente ..................... 600/543 |
| 5,433,922 A | 7/1995 | Parker et al. |
| 5,455,007 A | 10/1995 | Calvo et al. |
| 5,573,047 A | * 11/1996 | Akin .......................... 141/330 |
| 5,599,501 A | 2/1997 | Carey et al. .................. 422/64 |
| 5,728,954 A | 3/1998 | Uffenheimer |
| 5,935,523 A | 8/1999 | McCandless et al. |
| 5,942,694 A | 8/1999 | Robins et al. |
| 5,969,272 A | 10/1999 | Tanaka |
| 5,985,672 A | 11/1999 | Kegelman et al. ............. 436/50 |
| 6,190,617 B1 | 2/2001 | Clark et al. ................. 422/104 |
| 6,274,087 B1 | * 8/2001 | Preston et al. .............. 422/100 |

FOREIGN PATENT DOCUMENTS

| | | |
|---|---|---|
| EP | 0 289 789 A1 | 11/1988 |
| EP | 0 571 032 A1 | 11/1993 |

* cited by examiner

*Primary Examiner*—Jeffrey Snay
(74) *Attorney, Agent, or Firm*—Hogan & Hartson, L.L.P.; William H. May; D. David Hill (57) ABSTRACT

A piercing station for piercing sample container caps or thick stoppers. The piercing station has a structural frame with two vertical guide rods. A carriage assembly is slidably mounted on the guide rods and is further driven to move up and down along the guide rods. The carriage assembly carries a blade holder, which in turn holds a piercing blade assembly. The blade assembly includes a center blade and two cross blades interlocked together, such that the blade assembly has a generally modified "H"-shaped cross section for piercing a cap on the sample container. Lubricant left in or on the sample container cap by the piercing station reduces the force required by the sample probe to penetrate thick stoppers for sample aspiration and level sensing. The "H"-shaped cut helps to equalize the pressure in the sample container during sampling, so that clot detection is more effective.

53 Claims, 8 Drawing Sheets

CAP PIERCING STATION FOR CLOSED CONTAINER SAMPLING SYSTEM

BACKGROUND OF THE INVENTION

1. Area of the Art

The present invention relates generally to closed container sampling systems, such as clinical chemistry analyzers, and, more specifically, to piercing stations for a closed container sampling system.

2. Description of the Prior Art

Clinical chemistry sampling and analyzing systems often use closed containers to contain samples to be analyzed. One of the initial and necessary functions of such sampling systems is to pierce the cap or stopper on closed containers in which the samples are contained to obtain an opening on the cap or stopper for the subsequent insertion of a sampling probe. This cap piercing function is often performed by a cap piercing station of the sampling system.

In conventional sampling systems, the cap piercing station often employs piercing blades that have an X-shaped cross-section. This type of conventional piercing blade with an X-shaped cross-section appears to be able to pierce through caps or stoppers that are relatively thin. However, there are several disadvantages of this conventional type of piercing blade with an X-shaped cross-section.

One of the major disadvantages of the conventional type of a piercing blade with an X-shaped cross-section is that it is not suitable for piercing thick (i.e., approximately ⅜") caps or stoppers that are made of rubber material or the like. When inserting a sampling probe into the X-shaped cut made on the cap or stopper, the probe requires too much force to penetrate, resulting in motion errors and stalling the stepper motor drive. In addition, during withdrawal of the blades and the probe, the container tends to be lifted up together with the blades or probe and is hard to be held down.

Another disadvantage of this conventional type of a piercing blade with an X-shaped cross-section is that when a sample probe is subsequently inserted through the X-shaped cut left on the cap or stopper, the sample probe tends to re-seal the cap or stopper. This changes the pressure profile inside the sample container (depending on the amount of sample in the container) which can compromise the aspiration of the sample and the clot detection system that relies on detecting pressure variations during the aspiration cycle.

A further disadvantage of this conventional type of piercing blades with an X-shaped cross-section is that a false level sense may be produced when a probe is inserted into the container through a pierced cap or stopper. Oftentimes, container caps or stoppers are made with button shaped silicone rubber pieces supported by metallic foil closures. While piercing blades with an X-shaped cross-section can punch through the metallic foil, they only cut the metallic foil with an X-shaped cut. When the sampling probe later passes through the cap or stopper to reach the sample, it often touches the foil and thereby triggers a capacitance shift, which produces a false level sense that causes the system to believe that the sample fluid level is reached before the sample probe really reaches the fluid level.

Therefore, it is desirable to provide a piercing station with piercing blades of a new design that can reliably pierce thick caps or stoppers made of rubber or like materials and can also overcome the disadvantages of the conventional type of piercing blades with an X-shaped cross-section.

SUMMARY OF THE INVENTION

The present invention is directed to a piercing station for a closed container sampling system, such as a clinical chemistry analyzer.

It is one of the primary objects of the present invention to provide a piercing station for a closed container sampling system, such as a clinical chemistry analyzer. The piercing station utilizes newly designed and constructed piercing blades that can reliably pierce thick caps or stoppers made of rubber or like materials and can also overcome the disadvantages of the conventional type of piercing blades with an X-shaped cross-section.

The cap piercing station of the present invention utilizes piercing blades having an H-shaped cross-section, which cut an H-shaped opening in a cap or stopper on the top of a sample container. When a sampling probe is subsequently inserted, it stretches the opening into an eye-shaped opening, which provides the necessary ventilation for pressure equalization.

The cap piercing station of the present invention is further designed to work with handling racks that contain different sized containers and employs a cap presence sensor for detecting whether a cap or stopper is present at the top of a container for piercing. It also utilizes a shuttle mechanism for washing the blades between each piercing operation to eliminate carry-over contamination between sample containers. In addition, it incorporates a hydro-pneumatic lubrication and washing mechanism for lubricating and washing the blade between each piercing operation. The piercing station is also well-suited for use in an existing CTS system.

These and other objects and advantages are achieved in a piercing station that includes a structural frame having two vertical guide rods and a carriage assembly slidably mounted on guide rods. A step motor is provided to drive a lead screw, which in turn drives the carriage assembly to move up or down along the guide rod(s). A blade holder is mounted on the upper end of the carriage assembly. An alignment block assembly, which is independent of the carriage, slides along the guide rods, and is lifted and lowered by the vertical motion of the carriage assembly. The blade holder holds a piercing blade assembly, which includes a center blade with two parallel rows of three lengthwise slots, and two cross blades, which interlock with the center blade in its slots, respectively, such that the blade assembly has a generally modified H-shaped cross-section for piercing a thick cap or stopper on a sample container. The alignment block assembly is biased by a return spring for holding the container down when the blade assembly is being withdrawn after piercing the cap or stopper. Mounted on the alignment block assembly and cantilevered over the sample container is an alignment arm assembly. The arm assembly has a wash tower and a wick holder, in turn, mounted to it, so that they are centered above the sample container station. The design is such that the blade assembly must pass through the inside of the wick holder, wick assembly, wash station (or "shower"), and through the cap or stopper of the sample container, if appropriate. Included on the arm assembly is a cap sensor, which determines whether or not there is a cap present, or if it is merely an open tube. The arm centers the tube (regardless of cap outer diameter) so that the subsequent cut is aligned with the tube center. Another sensor determines the point of vertical contact between the arm and the stopper and, thus, the height of the tube. A hydro-pneumatic system provides the metered lubrication and washing of the blades, after piercing a sample cap. Two fittings attach to the wick holder. The fitting supplying the wash function feeds wash solution or D.I. water into the wash station via a set of nozzles. The other fitting feeds a small amount of silicone oil into a wick, through which the blades pass on each cycle.

The major unique and novel features of the cap piercing station of the present invention include the design and construction of piercing blades with an H-shaped cross-section, the use of a cap presence sensor, the ability to handle various sized containers, and the design and construction of the automated washing and lubrication mechanism for washing and lubricating the blades between piercing operations to prevent contamination caused by carry-over of samples.

Such an arrangement has been found to provide a number of advantages. As explained in greater detail below, the new piercing blades with an H-shaped cross-section are well-suited for piercing thick caps or stoppers made of rubber or like materials. A sampling probe can be easily inserted into the H-shaped cut made on the cap or stopper, thereby reducing motion errors and avoiding stalling the stepper motor drive. The blades and probe can also be easily withdrawn without lifting up the sample containers. The eye-shaped opening made by the insertion of the probe also provides adequate ventilation to maintain a proper pressure profile inside the container. It also avoids the problem of metallic foil closure, thereby eliminating any false level sense when the probe is inserted into the container through the pierced cap or stopper.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE PREFERRED EMBODIMENT OF THE INVENTION

The present invention provides a piercing station for a closed container sampling system, such as a clinical chemistry analyzer.

Figures 1, 2:
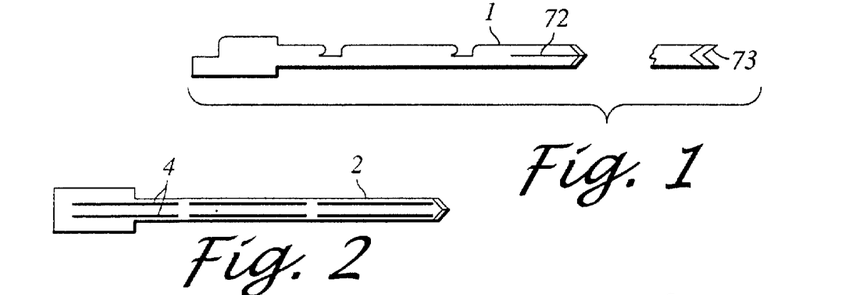
FIG. 1 is a side view of one of the two cross blades of the new piercing blades.
FIG. 2 is a side view of the center blade of the new piercing blades.
Figure 3:
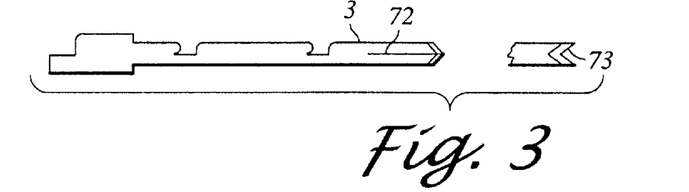
FIG. 3 is a side view of the other one of the two cross blades of the new piercing blades.

Referring to FIGS. 1, 2, and 3, there are shown three blades for assembling the new piercing blades with an H-shaped cross-section, including a first cross blade 1, a center blade 2 and a second cross blade 3. The center blade 2 has two parallel rows of lengthwise slots 4 for insertion of the two cross blades 1 and 3, respectively. Cross blades 1 and 3 are locked into these slots 4 of the center blade to assemble the new piercing blades. When assembled, the center blade 2 is on a plane perpendicular to the two cross blades 1 and 3, such that the assembled piercing blades have a modified, generally H-shaped cross-sectional configuration. In this arrangement, the center blade 2 and the cross blades 1 and 3 reinforce each other, forming a composite blade assembly, which is stiff and strong enough for piercing thick rubber caps or stoppers of the sample containers. The sharpened end of each blade is V- or inverted V-shaped, which reduces the piercing load on the cap to minimize the stretching of the cap during piercing. As an example, the center blade 2 and cross blades 1 and 3 may be made of Type 440 stainless steel hardened to Rc 58–60 and coated with titanium nitride. The hard coating such as titanium nitride on the piercing blades can help to maintain the cutting edges of the blades and increase the lubricity of the blades. Preferably, each blade has a thickness of 0.015". The cross blades may have small slots 72 at the piercing end for venting the sample container. An alternate inverted V point 73 may be used on the cross blades.

Figure 4:
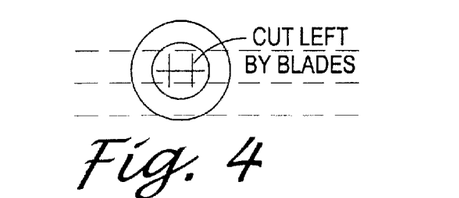
FIG. 4 is a top view of the H-shaped cut made by the new piercing blades.
Figures 5, 6:
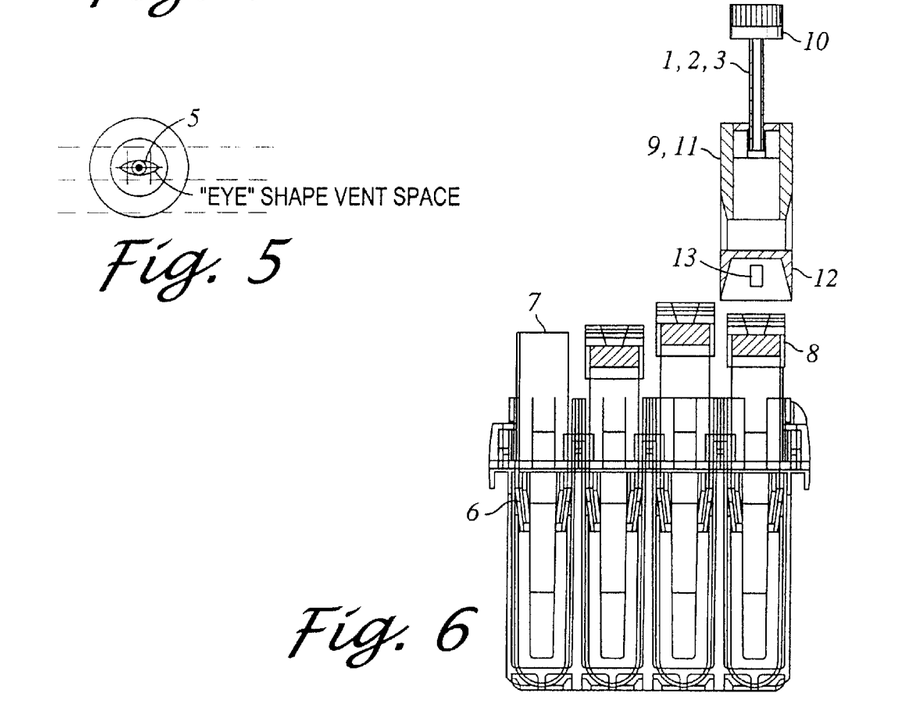
FIG. 5 is a top view of the eye-shaped opening stretched by the insertion of a sampling probe into the H-shaped cut made by the new piercing blades.
FIG. 6 is a side view of a rack with sample containers of various configurations, showing the piercing station of the present invention as suitable to work with such containers.

Referring to FIGS. 4 and 5, there is shown a modified, generally H-shaped cut made by the piercing blades of the present invention on a thick rubber cap or stopper of a sample container. When a sampling probe 5 is inserted through the H-shaped cut, the probe 5 will stretch the cut into an eye-shaped opening. This eye-shaped opening will provide a more adequate and reliable ventilation during the sample cycle, so that obstruction detention and sample aspiration meet the system requirements.

Referring to FIG. 6, there is illustrated the piercing station of the present invention that is capable of handling sample containers of various configurations or conditions held in a rack 6. For example, rack 6 may have sample containers of different heights or containers that are "open," i.e., without a cap or stopper, such as the one shown at 7, or containers that are "closed," i.e., with a cap or stopper, such as the one shown at 8. In order to handle either "open" or "closed" sample containers that may further have different heights, the piercing station of the present invention comprises a single piercing station 9, which includes a blade holder 10 for holding the piercing blades assembled by blades 1, 2, and 3, a blade shower 11, an alignment arm 12, and a trigger device 13. The structures and functions of these component parts will be described in detail below.

Figure 7:
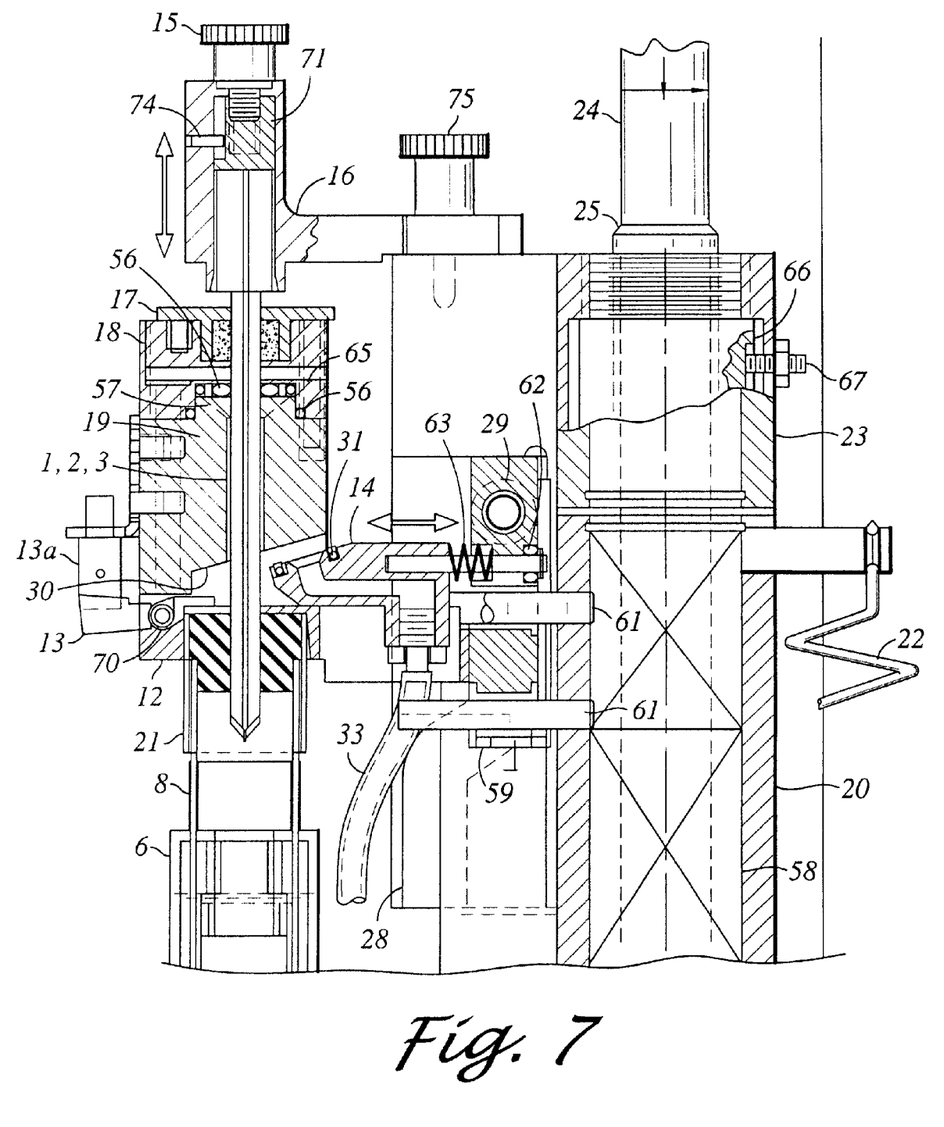
FIG. 7 is a side view schematic of a shuttle mechanism of the piercing station of the present invention with the shuttle in an "open" position during the piercing cycle.
Figure 8:
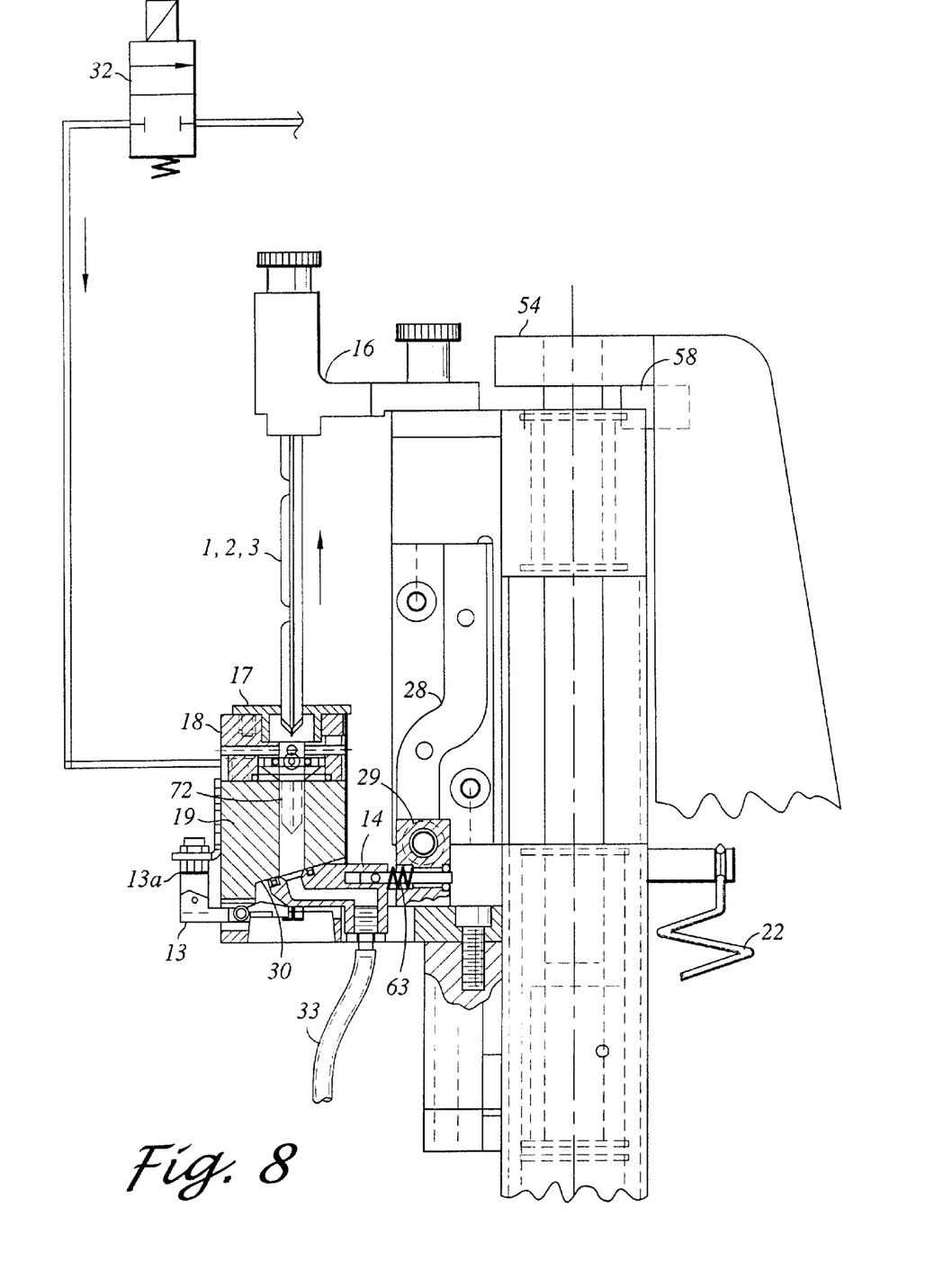
FIG. 8 is a side view schematic of the shuttle mechanism of the piercing station of the present invention with the shuttle in a "closed" position during the washing cycle.

Referring to FIGS. 7 and 8, there is shown a shuttle mechanism of the piercing station of the present invention.

The shuttle mechanism includes a shuttle 14 shown in an "open" position in FIG. 7, out of the way of the blades 1, 2, and 3 during the piercing cycle, and also shown in a "closed" position in FIG. 8, covering the sample containers during the washing cycle.

As shown in detail in FIGS. 7 and 8, a captive knurled screw 15 is used to hold the blades assembled in place in the blade holder 16. The blades pass through the wick assembly 17, through a wick holder 18, through the wash tower 19, past the shuttle 14 and through the alignment arm, where the piercing of the cap or stopper 21 takes place.

The trigger 13 is in its initial state (assisted by a torsion spring), as shown in FIG. 8. When there is no cap or stopper present on top of a sample container (i.e., the sample container is "open"), the flag on the other end of the trigger blocks the light beam in the photoelectric switch 13a. However, when a sample container 8 is closed by a cap or stopper 21, a trigger 13 will be pushed up by the cap or stopper 21, as shown in FIG. 7. The motion of the trigger 13 in turn unblocks the light beam in the photoelectric switch 13a to inform the control circuitry that there is a cap or stopper 21 to be pierced. The trigger 13 pivots on a trigger pin 64 and a pair of bushings 68 (see FIG. 9). The trigger 13 is biased by a torsion spring 70, so that the photoelectric switch 13a beam is blocked initially.

The blades 1, 2, and 3 and blade holder 16 are mounted on the carriage assembly 23, which rides up and down on two parallel guide rods 24. The alignment block assembly 20 moves with the carriage assembly 23. The alignment block assembly 20 has a strong return spring 22, which holds the container 8 down in rack 6, while the blades are being withdrawn after piercing.

As shown in FIG. 8, the shuttle 14 closes during the upward motion of the carriage assembly 23 carrying the piercing blades. A cam groove link 28 is mounted on the carriage assembly, which drives the shuttle in and out through a roller 29. As the carriage assembly 23 travels about half way up, the shuttle 14 closes and makes a seal against the inner tapered surface 30 of the wash tower 19 by means of an o-ring or quad-ring seal 31. A wash valve 32 (see FIGS. 8 & 10), which feeds the wash inlet 55 to the wash tower 19, is turned on. This action sends pressurized wash solution into an annular space 65 formed between the wick holder 18 and the wash tower 19, between two o-ring seals 56. This annular space feeds six downwardly aimed nozzles 57, sending a spray of wash solution (for example, water) onto the piercing blades. At about the same time (or slightly before), a vacuum is introduced at the waste outlet 33 to prevent the wash solution and/or waste products from splattering against the inside of the wash tower 19 and from introducing possibly harmful aerosols into the air.

Other elements shown in FIGS. 7 & 8 are the guide rods 24, which maintain the alignment of the carriage 23, the alignment block 20, and the frame 54. The carriage 23 and alignment block 20 each contain four linear ball bearings 58, which ride on the guide rods 24. The shuttle 14 is driven horizontally in and out of the wash tower 19 by the guide block 59, which travels on two horizontal guide pins 61. The shuttle 14 is mounted to the guide block 59 by means of a shuttle guide shaft 62, with a compression spring 63 between the shuttle 14 and the guide block 59. The spring provides the appropriate pre-load and compliance when the seal 31 is seated against the inclined surface 30 of the wash tower 19.

FIG. 7 shows the leadscrew/leadnut assembly 25 threaded into the top end of the carriage assembly 23, so that the notch 66 in the leadnut is aligned with the set screw 67, which prevents rotation of the leadnut.

A safety feature is shown in FIG. 7 to assure that the field engineer or the customer may safely remove worn blades and install new blades without special tools. The blade holder 16 is designed to be removed as a unit by loosening the knurled, captive screws 75. It makes a good handle while transporting the old blades to a sharps container. The blade assembly, which will be discarded, consists of the 3 blades 1, 2, and 3 and a blade clamp 71, which may be fabricated as an inexpensive molded part (alternatively, the clamp may be machined from aluminum bar stock). It has a threaded insert in the top, a slot on one side, which guides the blade assembly over a guide pin 74, and three slots (one for each blade) for proper blade orientation. Finger-tightening the knurled, captive, spring-loaded screw 15 draws the blade assembly and clamp 71 up into the cavity in the holder 16 and squeezes the blades tightly in their slots, similar to a collet used on a milling machine for various cutting tools. To dispose of the blade assembly, the blade holder is held over the sharps container, while the knurled screw 15 is loosened by hand. After loosening the screw 15, a push down on the head of the screw will dislodge the blade assembly, allowing it (clamp and blades) to fall into the sharps container. A new set of blades and the clamp are installed in reverse sequence. The blade sides may be safely handled as there are no sharp edges. The points should be covered for shipping, storing, and handling. This cover may be removed once the blades are properly installed in the holder 16.

FIG. 8 shows a phantom view of the blade assembly 72 inside the wash tower 19, on its way to the "home" position, after having pierced a thick stopper. At about this position, the wash solution can safely be admitted to the wash tower for washing the now contaminated blade assembly by turning on the valve 32, since the shuttle 14 is now back in its sealed position with the vacuum on.

Figure 9:
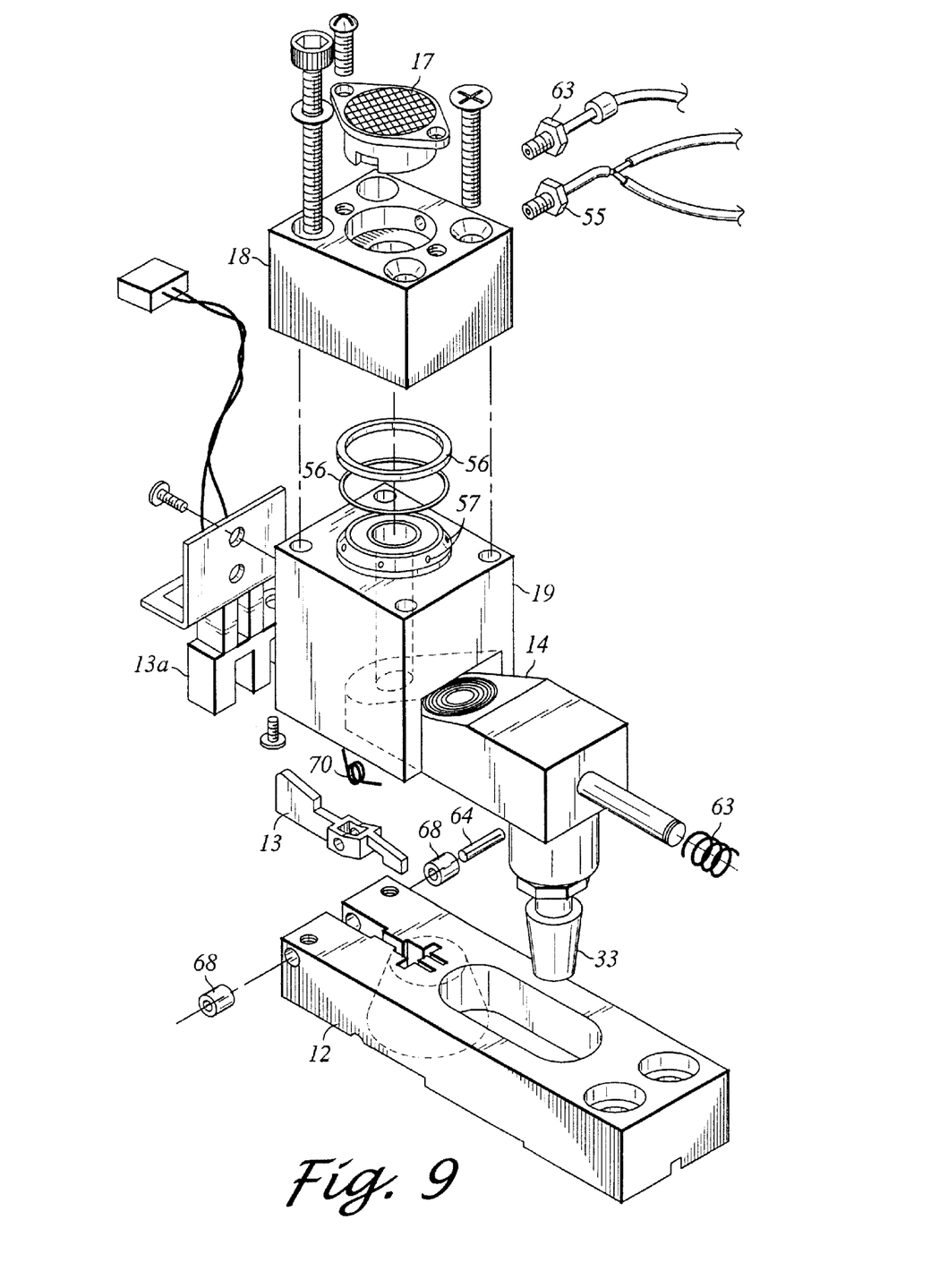
FIG. 9 is an exploded view of the alignment arm assembly of the piercing station of the present invention.

FIG. 9 is an exploded view of the alignment arm assembly showing some of the elements involved in the washing and lubrication of the blades. The oil inlet 63 meters the oil into the wick assembly 17. The wash inlet 55 provides wash solution for the probe wash function.

Figure 10:
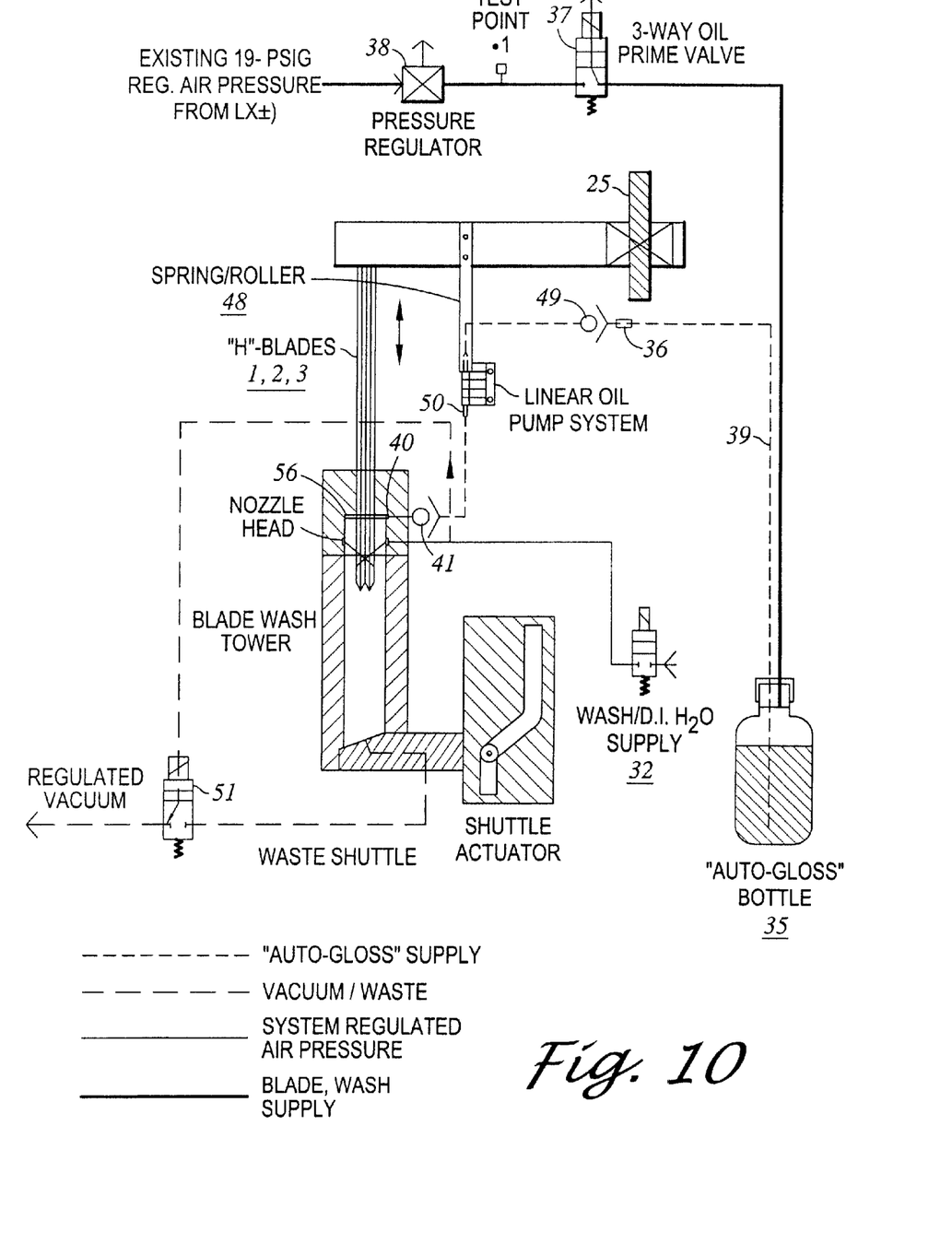
FIG. 10 is a schematic of a lubrication and washing hydro-pneumatic system of the piercing station of the present invention.
Figure 11:
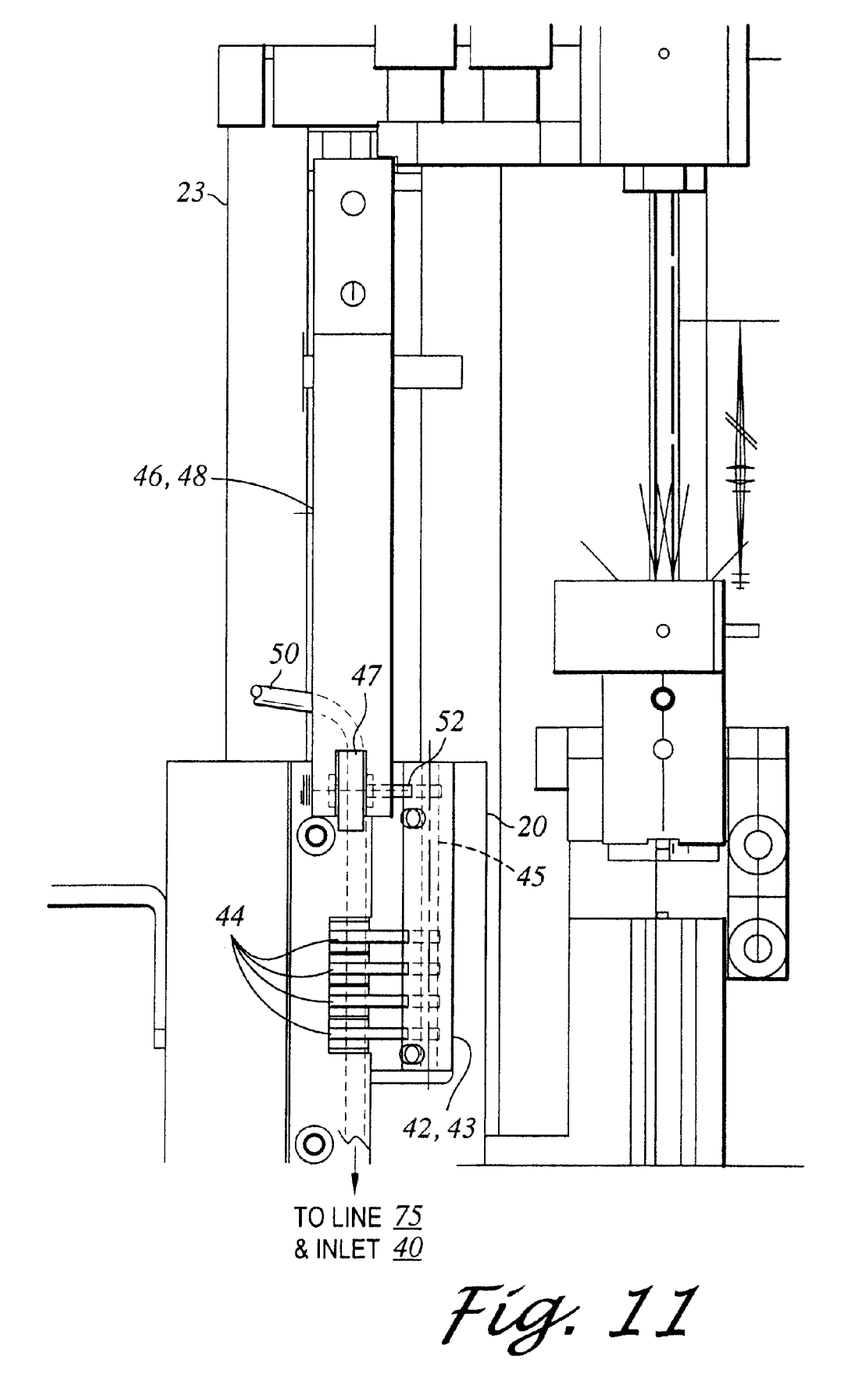
FIG. 11 is a front view of the lubrication pump mechanism of the piercing station of the present invention.

Referring to FIGS. 10 and 11, there is shown a lubrication and washing hydro-pneumatic system of the piercing station of the present invention, and an oil dispenser of the lubrication and washing hydro-pneumatic system. The lubrication and washing hydro-pneumatic system is designed to provide the appropriate amounts of lubrication and washing, and for handling waste from the blade cleaning process. It includes a bottle of silicone oil 35 with a sealed cap. A hose and a pick-up straw are plumbed from the oil bottle 35 to the inlet of the oil dispenser 36.

In order to accomplish a full system prime, such as with a brand new unit, or if the oil bottle is emptied, and/or air is allowed in the oil supply line, the carriage must be moved downward slightly, to remove the squeeze from the elastic tubing, after which it is returned to the "home" position.

To prime the oil line 39 at start up, system air pressure is applied to the oil bottle 35 via a pressure regulator 38 and a 3-way valve 37. The 3-way valve is plumbed with the common port connected to the bottle 35 and the normally closed port connected to the air supply coming from the pressure regulator 38. The normally open port is vented to the atmosphere. Because the bottle cap is sealed, when the valve 37 is switched on, the air pressure forces the oil through the straw, into the oil supply line 39 feeding the oil dispenser, the wick holder oil inlet 40 and into the oil wick 56. Because the shuttle 14 is in its "closed" position, the vacuum system may be activated at this time to remove any excess lubricant from the blade wash tower 19 in case the wick becomes over-saturated. The air pressure may be adjusted at the pressure regulator 38 to optimize the flow rate of the oil during the priming action. The system is now primed and the 3-way valve 37 is switched off—allowing the oil bottle to vent off pressure and thus stop the oil flow. To prevent siphoning of oil back into the bottle, a series of two check valves are installed, one upstream 49 of the oil dispenser and one downstream 41, close to the oil inlet port.

Referring to FIG. 11, the oil dispenser 42 uses linear peristaltic action to supply a predetermined amount of lubricant to the wick to replace that which is used during each "wiping" action of the blades as they reciprocate through the wick during piercing. The main pump body 43 is mounted on the alignment block 20. Mounted in the pump body 43, and captured by a pin 45, are four fingers 44 located adjacent to one another and at right angles to the elastic tube 50, which is routed under the fingers, between the fingers and the alignment block surface. The fingers are depressed sequentially by the action of a cantilevered spring 46, with a ball bearing 47 at one end, or some other kind of roller. The spring assembly 48 is mounted to the carriage 23, which also holds the blade assembly. The elastic tubing 50 is squeezed during each up and down cutting or priming cycle of the carriage 23, relative to the alignment block 20, which delivers the appropriate amount of oil to the system. The amount of oil delivered depends on the width and number of the fingers, and the cross-sectional area of the elastic tubing.

Backflow of the oil during the up stroke of the carriage 23, which would normally reverse the direction of the fluid flow, is prevented by the check valves 41 & 49 in the oil feed line. Unwanted pressure spikes caused by this reversal (since no fluid flow takes place) is absorbed by the cantilevered spring and the elasticity of the pump tubing. Thus, flow only occurs in the preferred direction.

To assist the check valve action during the time when the system is off-line, a fifth finger 52 is provided, which squeezes off the elastic tubing when the carriage 23 is in its "home" position. Although nearly all check valves exhibit some amount of leakage in the back check direction, this prevents any unwanted back siphoning of the oil out of the line into the bottle. This also eliminates having to re-prime the line each day.

The pump only works when there is relative motion between the carriage 23 and the alignment block 20, i.e., a complete cutting cycle. This normally occurs only when there is a closed sample tube 8 in a sample rack 6 under the piercing station. Therefore, when no tube is present in the sample rack 6 or a sample tube is presented which does not require piercing (such as an open or pre-cut tube), the cap detection trigger does not move, and the piercing cycle is aborted, and no oil is delivered.

In the event that a "miniprime" needs to be done (which may be required after the system is inactive for a period of time and the wick tends to dry out), a stop block 53 (attached to the frame 54) causes the alignment block 20 to stop on its way down with the carriage 23. The carriage 23 is allowed to finish its oil delivery stroke. The stop block 53 is located below the shortest expected tube height. The software normally does not permit the carriage to move this far down unless a "miniprime" is requested. With the stop block feature, a sample rack need not be present to do a "miniprime."

Figure 12:
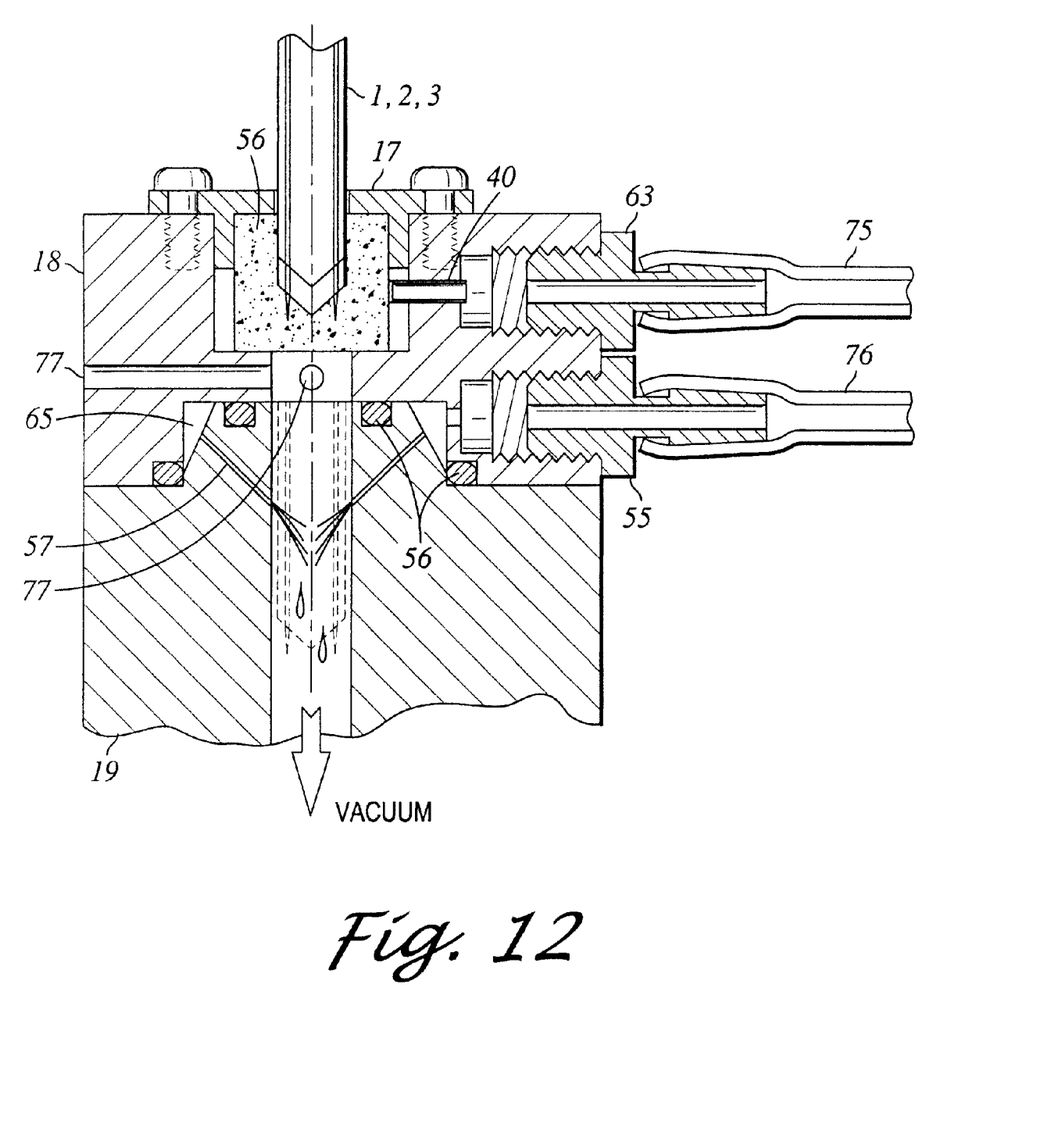
FIG. 12 is a cross section of the wash tower and wick holder.

Referring to FIG. 12, there is shown a wick assembly 17 of the piercing station of the present invention. The wick assembly 17 is detachably mounted on the wick holder 18 for easy maintenance and replacement. The wick assembly holds the wick 56, which is preferably a circular shaped pad made from some woven and absorbent fabric material. It forms a reservoir, which holds a small quantity of lubrication oil in contact with the blades. The oil enters the wick space through the port 63 in the wick holder. The oil delivery tube 75 comes from the outlet of the linear pump 42. The wick is subject to normal wear and tear and is, therefore, contained in one disposable assembly.

The wash delivery tube 76 is connected to the 2-way valve 32. The inlet fitting 55 for the wash is located in the wick holder 18 and the wash enters the annular space 65 (which is isolated by seals 56) to feed the nozzles 57 in the wash tower 19. The six nozzles 57 are currently aimed to hit all the exposed corners and surfaces of the blades 1, 2, and 3. Vent holes 77 admit ambient air during the wash/vacuum cycle to prevent a large pressure gradient from building up between the wick 56 and the vacuum source. This tends to dry out the wick.

Figure 13:
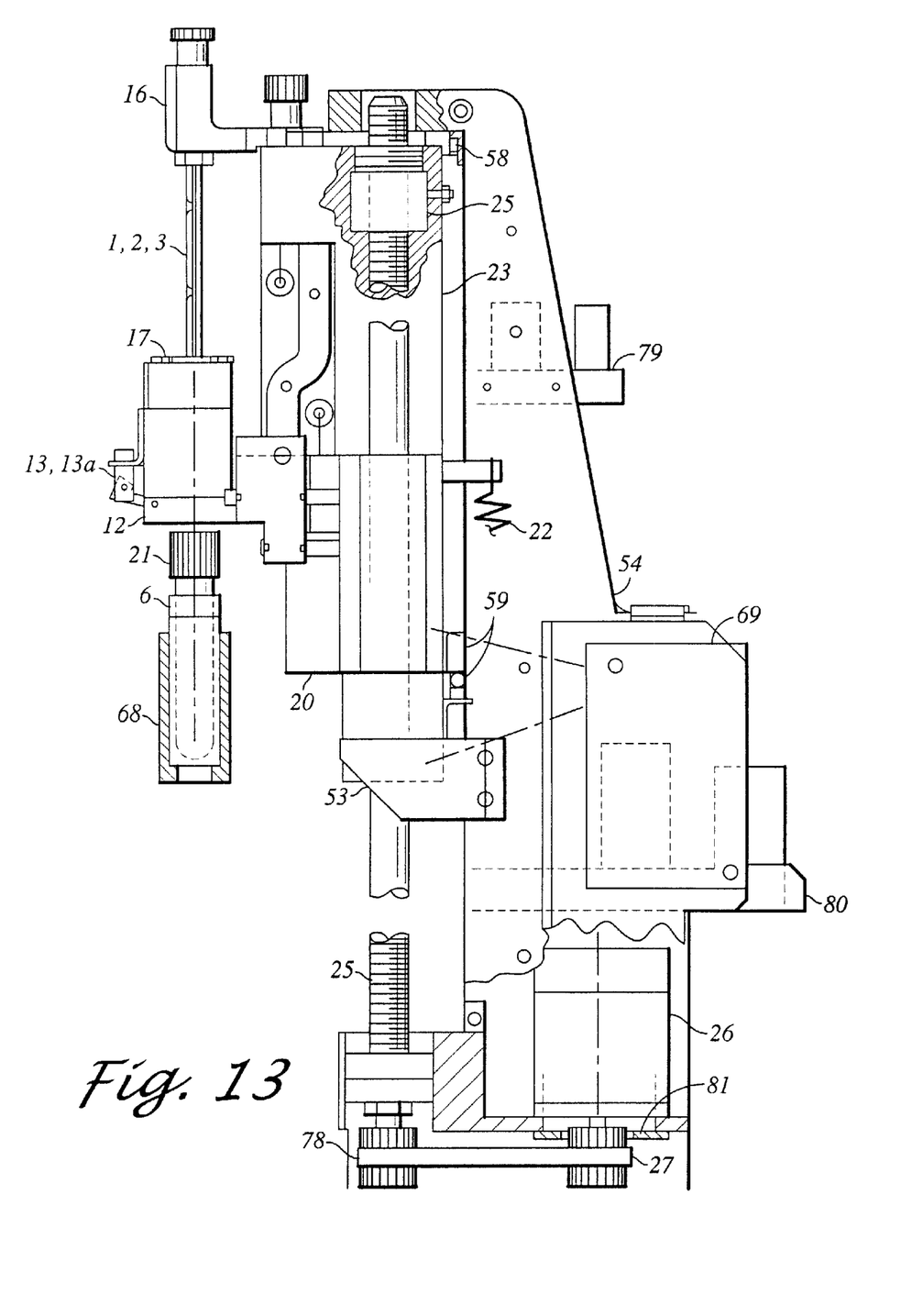
FIG. 13 is a side view of the piercing station of the present invention.

Referring to FIG. 13, there is shown the set-up arrangement of the piercing station of the present invention. The carriage assembly 23 is driven by a lead screw 25 terminating in a grooved pulley 78, which in turn is driven by a stepper motor 26 through a belt 27. The motor 26 mounts to the motor mounting plate 81 for a belt tension adjustment. A "home" sensor/flag 58 is provided at the top of the carriage travel. A container height sensor/flag 59 is installed between the carriage assembly 23 and the alignment block assembly 20, which is used to measure the height of the sample container that comes in contact with the alignment block assembly 20. The piercing station is supported by a frame 54. The oil dispenser 42 is located at the front of the alignment block 20 and the spring/roller mounted on the carriage assembly (see FIG. 11). The sample rack 6 with sample containers is guided into the piercing station by rails 68. A bar code reader 69 is provided to scan incoming racks, which determines whether or not the sample containers in a particular rack should be pierced. The upper valve assembly 79 contains valves 32 and 37. The lower valve assembly 80 contains a valve 51 and a pressure regulator 38.

The piercing station of the present invention has many advantages. The new piercing blade assembly design with multiple interlocked blades forming a stiff and durable piercing blade assembly with minimum bending can reliably pierce a thick (typically ⅜") rubber cap or stopper in the top of a sample container made of either glass or plastic without leaving debris or breaking the container. If the blades do come in contact with the sample inside the container, the blades are washed between each sample, so carry-over is minimal. The lubed piercing blades with an H-shaped cross-section can reduce the amount of vertical force required to pierce a thick cap or stopper, which prevents jamming the cap or stopper into the sample container and also reduces the retraction force required to strip the cap or stopper from the piercing blades. The H-shaped cut made by the new blades allows adequate ventilation during sample probe entry, so that obstruction detection and sample aspiration meet the system requirements. Additional vertical slots in the cross blades help to vent the tube at the piercing station. The cut made in the cap or stopper also allows multiple penetrations of the sampling probe without dislodging pieces of rubber or creating excessive debris.

The station has a washing system that cleans the blades between sample containers to eliminate carry-over contamination. It also has a lubrication system that lubricates the blades, which reduces force on the blades during the piercing operation and also leaves a small amount of lubricating oil on the pierced cap or stopper to reduce the force required by the sample probe to penetrate into and retract from the pierced cap or stopper later in the cycle. The oil dispenser can accurately dispense a fixed volume of oil in each cycle, without the complexity of a syringe pump that typically requires added motors.

The station can automatically distinguish between an "open" or a "closed" container. It also has a container height detection feature which determines whether a container is within the required range for piercing.

The set up and installation of the new piercing station is also safe and easy. The piercing station of the present invention is interchangeable with an existing Closed Tube Sampling (CTS) system, commercially available from Beckman Coulter.

The foregoing is meant to illustrate, but not to limit, the scope of the invention. Indeed, those of ordinary skill in the art can readily envision and produce further embodiments, based on the teachings herein, without undue experimentation.

It is to be understood that the form of the system depicted in FIGS. 1 through 12 has been chosen only for the purpose of describing a particular embodiment and function of the invention, and that the arrangement of the invention can be addressed in various ways and incorporated in other types of devices, all of which will be evident to those working in the art.

It is to be understood that the particular arrangement of the piercing station of the present invention may vary, depending on the sampling system incorporated or working together with, but that the determination of necessary variation is well within the skill of the art in view of the instant disclosure.

Suitable components that are commercially available would be known to those of ordinary skill in the art in view of this disclosure.

It is further understood that any comparable means of accomplishing this goal is within the scope of this invention.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for piercing container caps, comprising:
   a) a blade assembly, including a center blade and two cross blades interlocked together, such that the blade assembly has a generally modified H-shaped cross-section; and
   b) means for moving said blade assembly to pierce a cap on a container.

2. The apparatus as defined in claim 1, wherein said center blade further has at least two parallel lengthwise slots for interlocking attachment of said two cross blades.

3. The apparatus as defined in claim 1, wherein each said center and cross blades has a generally V- or inverted V-shaped piercing end for spreading the load across the width of each blade.

4. The apparatus as defined in claim 1, wherein said means for moving said blade assembly further comprises:
   a) a structural frame having at least one guide rod;
   b) a carriage assembly slidably mounted on said guide rod;
   c) means for driving said carriage assembly to move along said guide rod; and
   d) a support arm carried by and moving with said carriage assembly for holding said blade assembly.

5. The apparatus as defined in claim 4, wherein said means for driving said carriage assembly further comprises a lead screw for driving said carriage assembly and a motor for driving said lead screw.

6. The apparatus as defined in claim 4, further comprising an alignment block assembly also carried by and moving with said carriage assembly and further biased by a return spring for holding said container down when said piercing blade assembly is being withdrawn after piercing said cap.

7. The apparatus as defined in claim 1, further comprising means for washing said blade assembly.

8. The apparatus as defined in claim 7, wherein said means for washing said blade assembly further comprises a wash tower having a chamber for said blade assembly to pass through.

9. The apparatus as defined in claim 8, wherein said means for washing said blade assembly further comprises a shuttle mechanism mounted below said wash tower and having a shuttle movable between an open position for allowing said blade assembly to pass and a closed position for sealing off said wash tower after each piercing operation when said blade assembly is being washed.

10. The apparatus as defined in claim 9, wherein said shuttle is driven horizontally by a cam through the motion of said carriage assembly.

11. The apparatus as defined in claim 8, wherein said means for washing said blade assembly further comprises a series of nozzles aimed at said blade assembly and angled down, said nozzles being machined into an upper end of said wash tower for cleaning and washing said blade assembly.

12. The apparatus as defined in claim 1, further comprising means for lubricating said blade assembly before each piercing operation.

13. The apparatus as defined in claim 12, wherein said means for lubricating said blade assembly further comprises a container for containing a lubricant, a hydro-pneumatic system for pressurizing said container for priming with said lubricant, and a precision linear pump for dispensing said lubricant.

14. The apparatus as defined in claim 12, wherein said means for lubricating said blade assembly further comprises a replaceable soft and absorbent pad arranged in contact with said blade assembly for applying said lubricant to said blade assembly.

15. The apparatus as defined in claim 1, further comprising means for sensing the existence of said cap on said container.

16. The apparatus as defined in claim 15, wherein said means for sensing the existence of said cap on said container includes a photoelectric sensor.

17. The apparatus as defined in claim 1, further comprising means for sensing the height of said container.

18. The apparatus as defined in claim 1, further comprising means for guiding a rack containing said containers.

19. The apparatus as defined in claim 18, further comprising means for ascertaining information of said rack.

20. An apparatus for piercing caps on containers containing chemical samples, comprising:
   a) a structural frame having at least one vertical guide rod;
   b) a carriage assembly slidably mounted on said guide rod;
   c) means for driving said carriage assembly to move up or down along said guide rod;

d) a support arm carried by and moving with said carriage assembly;

e) a piercing blade assembly held by said support arm and including a center blade and two cross blades interlocked together, such that the piercing blade assembly has a generally modified H-shaped cross-section for piercing a cap on a sample container;

f) an alignment block assembly also carried by and moving with said carriage assembly and further biased by a return spring for holding said sample container down when said piercing blade assembly is being withdrawn after piercing said cap;

g) a wash tower mounted on said alignment block and having a chamber for said blade assembly to pass through;

h) means for washing said blade assembly; and i) means for lubricating said blade assembly.

21. The apparatus as defined in claim 20, wherein said means for driving said carriage assembly further comprises a lead screw for driving said carriage assembly and a motor for driving said lead screw.

22. The apparatus as defined in claim 20, wherein said center blade further has at least two parallel lengthwise slots for interlocking attachment of said two cross blades.

23. The apparatus as defined in claim 20, wherein each said cross blade further has at least one vertical slot for venting between inside of said sample container and outside ambient pressure during piercing.

24. The apparatus as defined in claim 20, wherein each said center and cross blades has a generally V- or inverted V-shaped piercing end for spreading the load across the width of each blade.

25. The apparatus as defined in claim 20, further comprising an alignment block assembly also carried by and moving with said carriage assembly and further biased by a return spring for holding said container down when said piercing blade assembly is being withdrawn after piercing said cap.

26. The apparatus as defined in claim 20, wherein said means for washing said blade assembly further comprises a shuttle mechanism mounted below said wash tower and having a shuttle movable between an open position for allowing said blade assembly to pass and a closed position for sealing off said wash tower after each piercing operation when said blade assembly is being washed.

27. The apparatus as defined in claim 20, wherein said means for washing said blade assembly further comprises a series of nozzles aimed at said blade assembly and angled down, said nozzles being machined into an upper end of said wash tower for cleaning and washing said blade assembly.

28. The apparatus as defined in claim 20, wherein said means for lubricating said blade assembly further comprises a container for containing a lubricant, a hydro-pneumatic system for pressurizing said container for priming with said lubricant, and a precision linear pump for dispensing said lubricant.

29. The apparatus as defined in claim 20, wherein said means for lubricating said blade assembly further comprises a replaceable soft and absorbent pad located inside said wash tower and arranged in contact with said blade assembly when it passes said wash tower for applying said lubricant to said blade assembly.

30. The apparatus as defined in claim 20, further comprising means for sensing the existence of said cap on said sample container.

31. The apparatus as defined in claim 30, wherein said means for sensing the existence of said cap on said sample container includes a photoelectric sensor.

32. The apparatus as defined in claim 20, further comprising means for sensing the height of said sample container.

33. The apparatus as defined in claim 20, further comprising means for guiding a rack containing said sample containers.

34. The apparatus as defined in claim 33, further comprising means for ascertaining information of said rack.

35. An apparatus for piercing caps on containers containing chemical samples, comprising:

a) a structural frame having two vertical guide rods;

b) a carriage assembly slidably mounted on said guide rods;

c) means for driving said carriage assembly to move up or down along said guide rod;

d) a support arm carried by and moving with said carriage assembly;

e) a piercing blade assembly held by said support arm and including a center blade with at least two parallel lengthwise slots and two cross blades interlocked with the center blade in its two slots, respectively, such that the piercing blade assembly has a generally modified H-shaped cross-section for piercing a cap on a sample container;

f) an alignment block assembly also carried by and moving with said carriage assembly and further biased by a return spring for holding said container down when said piercing blade assembly is being withdrawn after piercing said cap;

g) a wash tower mounted on said alignment block and having a chamber for said blade assembly to pass through;

h) means for washing said blade assembly after each piercing operation;

i) means for lubricating said blade assembly before each piercing operation;

j) means for sensing the existence of said cap on said sample container; and k) means for sensing the height of said sample container.

36. The apparatus as defined in claim 35, wherein said means for driving said carriage assembly further comprises a lead screw for driving said carriage assembly and a motor for driving said lead screw.

37. The apparatus as defined in claim 35, wherein each said center and cross blades has a generally V- or inverted V-shaped piercing end for spreading the load across the width of each blade.

38. The apparatus as defined in claim 35, wherein said means for washing said blade assembly further comprises a shuttle mechanism mounted below said wash tower and having a shuttle movable between an open position for allowing said blade assembly to pass and a closed position for sealing off said wash tower after each piercing operation when said blade assembly is being washed.

39. The apparatus as defined in claim 35, wherein said means for washing said blade assembly further comprises a series of nozzles aimed at said blade assembly and angled down, said nozzles being machined into an upper end of said wash tower for cleaning and washing said blade assembly.

40. The apparatus as defined in claim 35, wherein said means for lubricating said blade assembly further comprises a container for containing a lubricant, a hydro-pneumatic system for pressurizing said container for priming with said lubricant, and a precision linear pump for dispensing said lubricant.

41. The apparatus as defined in claim 35, wherein said means for lubricating said blade assembly further comprises a replaceable soft and absorbent pad located inside said wash tower and arranged in contact with said blade assembly when it passes said wash tower for applying said lubricant to said blade assembly.

42. The apparatus as defined in claim 35, wherein said means for sensing the existence of said cap on said sample container includes a photoelectric sensor.

43. The apparatus as defined in claim 35, further comprising means for guiding a rack containing said sample containers.

44. The apparatus as defined in claim 43, further comprising means for ascertaining information of said rack.

45. The apparatus as defined in claim 40, wherein said precision linear pump comprises a series of adjacent fingers mounted over a length of elastomeric tubing and orthogonal to said tubing, and a preloaded cantilevered spring with a roller on one end and mounted on said carriage assembly on the other end, such that said spring can roll over said fingers sequentially to squeeze out a precise amount of lubricant into a wick.

46. The apparatus as defined in claim 45, wherein said spring assembly is capable of rolling over said fingers of the precision linear pump upon the motion of said carriage assembly.

47. The apparatus as defined in claim 46, wherein the flow of said lubricant is directed by the down stroke of said carriage assembly, as controlled by two small-displacement, and non-elastomeric check valves located one on each side of said elastic tubing for blocking the flow in the reverse direction.

48. The apparatus as defined in claim 45, wherein the volumetric flow of said lubricant is primarily determined by the number and width of said fingers and the cross-sectional open area of said elastic tubing.

49. The apparatus as defined in claim 45, further comprises an additional finger over said tubing located at where said roller on said cantilevered spring comes to rest when said carriage assembly is at its home position, to prevent the backflow of said lubricant.

50. The apparatus as defined in claim 45, further comprises a stop block mounted to said frame for stopping downward travel of said alignment block at a predetermined point, while allowing said carriage assembly to keep moving, to create an oil pumping action during priming when no container is in position.

51. The apparatus as defined in claim 50, wherein a precise amount of oil is dispensed onto a wick, such that said blade assembly can pick up a portion of said amount of oil from said wick and transport said portion of said oil onto said cap of said sample container during piercing, and leaves part of said portion of said oil on said cap of said container after piercing because of the vacuum pre-existed in said container, which reduces the friction for insertion of a sample probe into said cap of said container during subsequent sampling.

52. The apparatus as defined in claim 38, further comprising a three-way valve connected to a system regulated vacuum source, said valve having a normally closed port plumbed to an outlet port of said shuttle mechanism to control the vacuum when said blade assembly is washed, and a normally open port plumbed to an inlet port of said wash station to remove remaining fluid after washing said blade assembly.

53. The apparatus as defined in claim 20, further comprising means for mounting said blade assembly to said supporting arm, which includes captive hardware designed for safe installation and removal of said blade assembly without special tools and allowing one-handed disposal of said blade assembly into a collector.

* * * * *